United States Patent [19]

Tsuji et al.

[11] 4,223,132
[45] Sep. 16, 1980

[54] SELECTIVE CONVERSION OF BENZYL ALCOHOL CARBOXYLATES TO THE FREE ACID FORM

[75] Inventors: Teruji Tsuji, Takatsuki; Mitsuru Yoshioka, Toyonaka; Takahiro Kataoka, Shiga; Yuji Sendo, Itami; Shoichi Hirai, Ibaraki; Takashi Maeda, Kobe; Wataru Nagata, Nishinomiya, all of Japan

[73] Assignee: Shionogi & Co., Ltd., Osaka, Japan

[21] Appl. No.: 818,597

[22] Filed: Jul. 25, 1977

Related U.S. Application Data

[63] Continuation-in-part of Ser. No. 773,962, Mar. 3, 1977, abandoned.

[30] Foreign Application Priority Data

Mar. 3, 1976 [JP] Japan .................................. 51-23602

[51] Int. Cl.$^2$ .......................................... C07D 501/04
[52] U.S. Cl. ........................................ 544/16; 544/21; 544/27; 544/28; 544/30; 544/26
[58] Field of Search ...................... 544/16, 27, 30, 28, 544/21, 26

[56] References Cited

U.S. PATENT DOCUMENTS

| | | | |
|---|---|---|---|
| 3,275,626 | 9/1966 | Morin et al. | 544/17 |
| 3,781,282 | 12/1973 | Garbrecht | 260/243 C |
| 3,799,924 | 3/1974 | Jackson | 260/243 C |
| 4,091,214 | 5/1978 | Hatfield | 544/30 |

*Primary Examiner*—Nicholas S. Rizzo
*Attorney, Agent, or Firm*—Birch, Stewart, Kolasch & Birch

[57] ABSTRACT

A process for preparing free carboxylic acids which comprises treating an optionally substituted benzyl ester with a Lewis acid, preferably in the presence of a cation acceptor, followed by hydrolysis, if required.

11 Claims, No Drawings

SELECTIVE CONVERSION OF BENZYL ALCOHOL CARBOXYLATES TO THE FREE ACID FORM

This application is a continuation-in-part of copending application, Ser. No. 773,962, filed on Mar. 3, 1977, now abandoned.

I. SCOPE

This invention relates to a process for removing a carboxy-protecting group. More specifically, it relates to a process for preparing free carboxylic acids by treating an optionally substituted benzyl ester of a carboxylic acid with a Lewis acid. Further, it relates to a process for preparing free carboxylic acids which are difficult to liberate from their protecting group by other methods, especially those of cephalosporins from their benzyl esters by treatment with a Lewis acid, followed by, if required, hydrolyzing the product.

The preferable process of this invention is shown by the following reaction scheme:

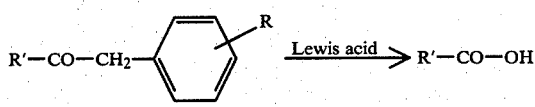

wherein
R'CO is a carboxylic acyl; and
R is as defined below.

A representative process of this invention is shown by the following reaction scheme:

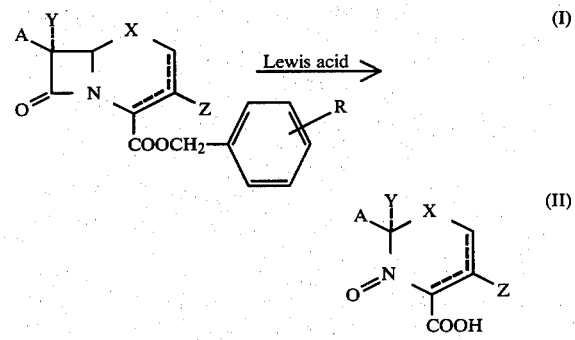

wherein
A is amino or protected amino;
R is hydrogen, $C_1$ to $C_5$ alkyl, $C_1$ to $C_5$ alkoxy, hydroxy, $C_5$ to $C_{10}$ aryloxy, $C_1$ to $C_{12}$ acyloxy, amino, $C_1$ to $C_5$ alkylamino, $C_1$ to $C_8$ acylamino, carboxy, $C_2$ to $C_6$ carbalkoxy, carbamoyl, or halogen;
X is oxygen, sulfur, or methylene;
Y is hydrogen or methoxy;
Z is hydrogen, $C_1$ to $C_5$ alkyl, $C_1$ to $C_5$ alkoxy, hydroxy, arylthio, $C_1$ to $C_{10}$ substituted amino, $C_1$ to $C_{10}$ substituted methyl or halogen; and
the broken line shows the presence of a double bond at position 2 or 3.

II. INTRODUCTION

In cephalosporin chemistry, conventional carboxy-protecting groups have been devised under limited conditions to avoid decomposition of the unstable β-lactam. Benzyl esters have been representative of these groups, of which catalytic hydrogenation has been used for deprotection. This procedure, however, requiring expensive catalysts and dangerous hydrogen, is unsuitable for large scale productions in a factory. Particularly, unsubstituted benzyl esters are difficultly removed by catalytic hydrogenation, and have not been used for production of β-lactam antibiotics.

The present inventors have found that carbobenzoxy and benzyl esters are readily cleaved by a Lewis acid to give the corresponding free acids.

This invention is based on these observations. As a result of this invention, benzyl esters are expected to be one of the most useful carboxy-protecting groups for cephalosporins.

It is understandable that the compounds easily decomposed by the conditions of reaction or working up of this process, e.g. penam compounds, cannot be treated according to the process of this invention, unless the decomposition is suppressed by modifying the said conditions.

SUBSTITUTED AMINO A

The substituted amino, A, can be a side chain of natural or synthetic penicillins and cephalosporins, It can be organic or inorganic acylamino, acylimino, hydrocarbylamino, sulfenylamino, silylamino, or an acid addition salt at the amino group.

Representative acyl groups for A can be selected from the following groups:
(1) $C_1$ to $C_{10}$ alkanoyl;
(2) $C_1$ to $C_5$ haloalkanoyl;
(3) azidoacetyl or cyanoacetyl;
(4) acyl groups of the following formula:

in which
Q and Q' each is hydrogen or methyl and
Ar is phenyl, dihydrophenyl, or monocyclic heteroaromatic groups containing from 1 to 4 hetero ring atoms selected from N, O, and/or S atoms, and each can optionally be substituted by an inert group, e.g., $C_1$ to $C_5$ alkyl, trifluoromethyl, cyano, aminomethyl, optionally protected carboxymethylthio, hydroxy, $C_1$ to $C_3$ alkoxy, $C_1$ to $C_{10}$ acyloxy, $C_7$ to $C_{10}$ aralkoxy, chlorine, bromine, iodine, fluorine, or nitro.
(5) (4-pyridon-1-yl)acetyl or (2-iminothiazolin-4-yl)acetyl;
(6) acyl groups of the following formula:

in which
Ar, Q, and Q' are as defined above and
G is an O or S atom.
(7) acyl groups of the following formula:

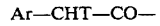

in which
Ar is as defined above and
T is
(i) hydroxy or $C_1$ to $C_{10}$ acyloxy;
(ii) carboxy, $C_2$ to $C_7$ alkoxycarbonyl, $C_2$ to $C_{15}$ aralkoxycarbonyl, $C_1$ to $C_{12}$ aryloxycarbonyl, $C_1$ to $C_7$ alkanoyloxy-$C_1$ to $C_3$ alkoxy-carbonyl, cyano, or carbamoyl;
(iii) sulfo or $C_1$ to $C_7$ alkoxysulfonyl;

(8) acyl groups of the following formula:

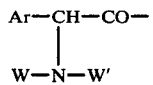

in which
Ar is as defined above and
W and W' each is hydrogen or an amino substituent including $C_2$ to $C_{10}$ alkoxycarbonyl, $C_3$ to $C_{10}$ cycloalkyl-$C_2$ to $C_3$-alkoxycarbonyl, $C_5$ to $C_8$ cycloalkoxycarbonyl, $C_1$ to $C_4$ alkylsulfonyl-$C_1$ to $C_4$-alkoxycarbonyl, halo-$C_1$ to $C_3$-alkoxycarbonyl, $C_1$ to $C_{15}$ aralkoxycarbonyl, $C_1$ to $C_{10}$ alkanoyl, or $C_2$ to $C_{15}$ aroyl, each optionally substituted by an inert group (e.g. hydroxy, $C_1$ to $C_5$ alkyl, $C_1$ to $C_{10}$ alkanoyloxy, halogen, $C_1$ to $C_3$ hydroxyalkyl, trifluoromethyl); pyronecarbonyl, thiopyronecarbonyl, pyridonecarbonyl, carbamoyl, guanidinocarbonyl, optionally substituted ureidocarbonyl (e.g. 3-methyl-2-oxoimidazolidin-1-ylcarbonyl, 3-methanesulfonyl-2-oxoimidazolidin-1-ylcarbonyl, 3-methylureidocarbonyl, 1-methylureidocarbonyl), optionally substituted aminooxalylcarbamoyl (e.g. 4-methyl-2,3-dioxopiperazin-1-ylcarbonyl, 4-ethyl-2,3-dioxopiperazin-1-ylcarbonyl), optionally substituted thioureidocarbonyl equivalents of the above ureidocarbonyl or aminooxalylcarbamoyl, or W, W', and the nitorgen atom combined together represent phthalimido, maleimido, or enamino derived from an enolizable carbonyl compound (e.g. $C_5$ to $C_{10}$ acetoacetates, $C_4$ to $C_{10}$ acetacetamides, acetoacetanilides, acetylacetone, acetoacetonitrile, α-acetyl-γ-butyrolactone, 1,3-cyclopentanedione);

(9) acyl groups of the following formula:

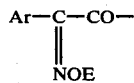

(in which
Ar is defined above and
E is hydrogen or $C_1$ to $C_5$ alkyl);

(10) 5-aminoadipoyl, N-protected 5-aminoadipoyl (protected by e.g. $C_1$ to $C_{10}$ alkanoyl, $C_1$ to $C_{10}$ aralkanoyl, $C_2$ to $C_{11}$ aroyl, $C_1$ to $C_5$ haloalkanoyl, or $C_2$ to $C_{11}$ alkoxycarbonyl), or
5-aminoadipoyl protected at the carboxy troup (protected by e.g. $C_1$ to $C_5$ alkyl, $C_2$ to $C_{21}$ aralkyl, $C_1$ to $C_{10}$ aroyl, $C_2$ to $C_{10}$ trialkylsilyl, $C_2$ to $C_5$ dialkyl-$C_1$ to $C_5$-alkoxysilyl, and
each protecting group for amino or carboxy can optionally be substituted by $C_1$ to $C_5$ alkyl, $C_1$ to $C_5$ alkoxy, halogen, or nitro; and
(11) acyl groups of the following formula:

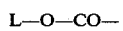

in which L is an easily removable and optionally substituted $C_1$ to $C_{10}$ hydrocarbyl group (e.g. t-butyl, 1,1-dimethylpropyl,
cyclopropylmethyl, 1-methylcyclohexyl, isobornyl, 2-$C_1$ to $C_2$-alkoxy-t-butyl, 2,2,2-trichloroethyl, benzyl, naphthylmethyl, p-methoxybenzyl, pyridylmethyl, diphenylmethyl).

Typical examples of Ar in said definitions include furyl, thienyl, pyrryl, oxazolyl, isoxazolyl, oxadiazolyl, oxatriazolyl, thiazolyl, isothiazolyl, thiadiazolyl, thiatriazolyl, pyrazolyl, imidazolyl, triazolyl, tetrazolyl, phenyl, pyridyl, pyrimidyl, pyrazinyl, pyridazinyl, triazinyl, dihydrophenyl, and each can optionally be substituted by halogen, $C_1$ to $C_5$ alkyl, hydroxy, $C_1$ to $C_5$ acyloxy, $C_7$ to $C_{15}$ aralkoxy (e.g. benzyloxy, methoxybenzyloxy, aminobenzyloxy), aminomethyl, $C_1$ to $C_5$ alkoxy and $C_7$ to $C_{12}$ aralkoxycarbonyl.

Alternatively, A can be a diacylamino group derived from $C_4$ to $C_{10}$ polybasic carboxylic acids.

Other amino-substituents for A include optionally substituted $C_1$ to $C_{20}$ hydrocarbyl (e.g. 1-carbethoxy-1-propen-2-yl, 1-carbamoyl-1-propen-2-1, 1-N-phenylcarbamoyl-1-propen-2-1, 1-propen-2-yl, 1-phenyl-1-penten-2-yl, methyl, t-butyl, trityl),
optionally substituted $C_1$ to $C_{15}$ hydrocarbylidene (e.g. methylidene, ethylidene, 1-halo-2-phenylmethylidene, 1-$C_1$ to $C_8$ alkoxyethylidene, 3,5-di-t-butyl-4-hydroxybenzylidene, o-hydroxybenzylidene), and $C_3$ to $C_{10}$ organic silyl (e.g. trimethylsilyl, methoxydimethylsilyl, dimethoxymethylsilyl) and $C_3$ to $C_{10}$ organic stannyl (e.g. trimethylstannyl).

A group convertible into amino or amido (e.g. azido, isocyanato, isocyano) is another member of A.

Two amino substituents in A can combine to form a ring.

Reactive A can be protected and afterwards de-protected by conventional methods.

When the products of this invention are intermediates for synthesizing other products, the substituents of the substituted amino A can usually be removed conveniently at any suitable state of the synthesis, and may be varied widely without changing the gist of this invention.

GROUP X

The group X is divalent oxygen, sulfur, or methylene, among which sulfur and oxygen are more preferable.

GROUP Y

The group Y is hydrogen or methoxy.

GROUP Z

The group Z is hydrogen, $C_1$ to $C_5$ alkyl (e.g. methyl, ethyl, propyl), a nucleophilic group, including halogen (e.g. chlorine, bromine), $C_1$ to $C_6$ alkoxy (e.g. methoxy, ethoxy, propoxy, isopropoxy, butoxy, isobutoxy, pentyloxy, cyclopentyloxy, hexyloxy, cyclohexyloxy, cyclopropylmethoxy), aralkoxy (e.g. benzyloxy, methoxybenzyloxy, aminobenzyloxy), $C_1$ to $C_5$ alkylthio (e.g. methylthio, ethylthio, propylthio, sec-butylthio), $C_1$ to $C_{10}$ arylthio (e.g. phenylthio, furylthio, thienylthio, pyrrylthio, oxazolylthio, isoxazolylthio, oxadiazolylthio, oxatriazolylthio, thiazolylthio, isothiazolylthio, thiadiazolylthio, triatriazolylthio, pyrazolylthio, imidazolylthio, triazolylthio, tetrazolylthio, pyridylthio, pyrimidylthio, pirazinylthio, pyridazinylthio, triazinylthio, and each can optionally be substituted by halogen, $C_1$ to $C_3$ alkyl, hydroxy, $C_1$ to $C_8$ acyloxy, $C_1$ to $C_5$ alkoxy, $C_7$ to $C_{10}$ aralkoxy (including benzyloxy, methoxybenzyloxy), aminomethyl, and substituted $C_1$ to $C_5$ alkyl including carboxymethyl, carboxyethyl, sulfoethyl, hydroxymethyl, carbamoylethyl, halopropyl), acylthio (e.g. formimidothio, acetylthio, benzoylthio), substituted amino (e.g. methylamino, dimethylamino, diethylamino, methylethylamino, phenyl-amino, nitrophenylamino, morpholino, piperidino), azido, thiocyanato, or $C_1$ to $C_3$ alkyl substituted by the said nucelophilic groups.

Reactive Z can be protected for the reaction, and afterwards deprotected by conventional methods at a suitable state of synthesis, if required.

III. PROCESS

The process of this invention is effected by bringing a starting benzyl ester into contact with a Lewis acid in a solvent, followed by, if required, hydrolysis of the product, and the product is isolated according to a conventional method.

(Temperature) The reaction is preferably carried out at from $-10°$ C. to $100°$ C., and more preferably at from $0°$ C. to $40°$ C.

(Lewis acid) The Lewis acids for this invention include boron trihalides (e.g. boron trichloride, boron tribromide, boron trifluoride), titanium tetrahalides (e.g. titanium tetrachloride, titanium tetrabromide), zirconium tetrahalides (e.g. zirconium tetrachloride, zirconium tetrabromide), tin tetrahalides (e.g. tin tetrachloride, tin tetrabromide), antimony halides (e.g. antimony trichloride, antimony pentachloride), bismuth trichloride, aluminum trihalides (e.g. aluminum trichloride, aluminum tribromide), zinc halides (e.g. zinc chloride, zinc bromide), ferric halide (e.g. ferric chloride, ferric bromide), and zinc sulfate.

(Solvent) The said solvents are conventional aprotic solvents including hydrocarbons (e.g. pentane, hexane, petroleum ether, benzene, toluene, xylene), halohydrocarbons (e.g. methylene chloride, chloroform, dichloroethane, trichloroethane, chlorobenzene), carbon disulfide, nitrohydrocarbons (nitromethane, nitrobenzene, nitrotoluene), or ethers (e.g. diethyl ether, methyl isobutyl ether, tetrahydrofuran, tetrahydropyran, dioxane, diphenyl ether, anisole), and mixtures thereof.

Less side reaction is observable when nitroalkane, carbon disulfide, halohydrocarbon, or ether solvents, or the mixtures thereof, are used as solvents.

Methylene chloride, anisole, or a mixture of methylene chloride and nitromethane or anisole is one of the most preferable solvents.

(Accelerator) The reaction is accelerated and controlled by the presence of a carbonium cation acceptor in the reaction medium. Representative of the accelerators are nucleophilic compounds e.g. anisole, phenol, nitrophenol, thiophene, etc.

(Most preferable condition) The reaction is preferably carried out by mixing 1.5 to 10 mole equivalents of a Lewis acid (particularly aluminum chloride), 1.5 to 10 mole equivalents of a carbonium cation acceptor (particularly anisole), and one mole equivalent of a starting benzyl ester (I) in a mixture of a nitroalkane (particularly nitromethane) or an aryloxyalkane (particularly anisole) or a haloalkane (particularly methylene chloride) (5:1 to 1:10, more preferably 1:1–1:4) at room temperature for 2 to 7 hours.

(Time) The speed of the reaction largely depends on the concentration of the starting benzyl ester, Lewis acid and cation acceptor, temperature, and solvent, but under favorable conditions, the reaction is complete within 1 to 24 hours. At room temperature in the presence of a cation acceptor, the reaction usually ends after 1 to 12 hours from the start.

(Hydrolysis) When the product is in the form of salt or organometallic ester derivatives, it can be hydrolyzed with acid (e.g. mineral acids, carboxylic acids, sulfonic acids, acidic ion exchange resins), or base (e.g. alkali metal hydroxides, alkali metal carbonates, basic ion exchange resins), preferably in the presence of water. When the cation acceptor is used, the product is in a salt form. When the cation acceptor is not used, the product can be in the form of an organometallic ester. Both of them can be hydrolyzed conveniently with an aqueous mineral acid (e.g. hydrochloric acid, sulfuric acid, nitric acid).

IV. WORKING UP OF THE REACTION MIXTURE

The resulting objective free acids can be separated from the reaction mixture containing solvents, unreacted materials, and by-products by means of conventional procedures such as adjustment of pH, extraction, recrystallization, absorption, concentration, and precipitation, and can be purified by means of recrystallization, reprecipitation, chromatography, washing, and drying.

One of the special problems for this invention is how to remove the reacted Lewis acid conveniently from the reaction mixture. Usually, Lewis acids or their derivatives dissolve in water with decomposition giving precipitates, an emulsion, or a sol. In such cases, acids can be added to the mixture to dissolve solid material, or a high porous polymer can be used to adsorb the higher molecular objective free acids.

V. ADDITIONAL STATEMENTS

The reaction may also be applied for removing other groups under the same condition (e.g. t-butoxycarbonyl or carbobenzoxy) when they exist together with the benzyl groups in the molecule to be deprotected. Such cases are also included within the scope of this invention.

The objective compounds thus prepared according to the present invention exhibit many uses such as antibacterial activity, and are used as medicines for combatting against bacterial infections. They also are useful intermediates for preparing useful antibacterial agents.

VI. EXAMPLES

The following examples are given to show in detail some of the specific embodiments of this invention. However, they are not given with any intention to restrict the scope of the invention. The abbreviations employed are commonly accepted ones.

EXAMPLE 1

To a solution of benzyl 7$\beta$-phenoxyacetamido-3-methyl-3-cephem-4-carboxylate (1.0 g) in methylene chloride (20 ml) is added a solution of aluminum chloride (961 mg) in nitromethane (20 ml) under ice cooling, and the mixture stirred for 5 hours at room temperature, diluted with ethyl acetate, washed with dilute hydrochloric acid, and extracted with 5% aqueous solution of sodium hydrogen carbonate. The extract is acidified with hydrochloric acid and extracted with ethyl acetate. The extract is washed with water, dried, and evaporated to yield a residue (1.03 g), which is recrystallized from a mixture of acetone and pentane to yield 7$\beta$-phenoxyacetamido-3-methyl-3-cephem-4-carboxylic acid. mp. 175°–177.5° C. Yield: 93.9%.

EXAMPLE 2

A solution of benzyl 7$\beta$-phenylacetamido-3-methyl-3-cephem-4-carboxylate (507 mg) in methylene chloride (10 ml) is cooled to about 0° C. and mixed with anisole (0.79 ml) and a solution of aluminum chloride (483 mg) in nitromethane (10 ml). The mixture is stirred for 4.5 hours at room temperature and mixed with ethyl acetate (50 ml) and dilute hydrochloric acid (20 ml). The organic layer is separated and extracted with 5% aqueous solution of sodium hydrogen carbonate. The extract is acidified with hydrochloric acid and extracted with ethyl acetate. The extract is washed with water, dried over sodium sulfate, and concentrated to give a residue (362 mg) which is crystallized from n-pentane (10 ml) to yield 7β-phenylacetamido-3-methyl-3-cephem-4-carboxylic acid (343 mg).

mp. 193°–196° C. Yield: 86.1%.

EXAMPLE 3

To a solution of benzyl 7β-amino-3-methyl-3-cephem-4-carboxylate (1.2 g) and anisole (5.2 ml) in methylene chloride (100 ml) is dropwise added a solution of aluminum chloride (3.11 g) in nitromethane (40 ml) under ice cooling, and the mixture stirred for 4.5 hours at room temperature, mixed with water (40 ml), and adjusted to pH 0.3 with 1 N-hydrochloric acid. The aqueous layer is separated, washed with ethyl acetate (30 ml), adjusted to pH 2.4 with an aqueous solution of sodium hydroxide and allowed to stand overnight at 0° C. The resulting crystals are collected by filtration to give 7β-amino-3-methyl-3-cephem-4-carboxylic acid (757 mg). Yield: 89.6%. This product was identical with an authentic specimen in NMR and IR spectra.

EXAMPLE 4

To a solution of benzyl 7β-amino-3-methyl-3-cephem-4-carboxylate (1.2 g) and anisole (5.2 ml) in methylene chloride (100 ml) is added a solution of titanium tetrachloride (2.6 g) in nitromethane under ice cooling, and the mixture stirred for 9.5 hours at room temperature. The reaction mixture is adjusted to pH 1 or less with diluted hydrochloric acid (70 ml), washed with ethyl acetate, and neutralized with 6 N-sodium hydroxide. The resulting titanium hydroxide is removed by filtration, and the filtrate concentrated under reduced pressure at a temperature below 50° C. The resulting crystals are collected by filtration to give 7β-amino-3-methyl-3-cephem-4-carboxylic acid (270 mg). Yield: 32%. This product was identical with an authentic specimen in NMR and IR spectra.

EXAMPLE 5

To a solution of cefalotin benzyl ester (480 mg) and anisole (650 mg) in methylene chloride (50 ml) is added a solution of aluminum chloride (400 mg) in carbon disulfide (20 ml), and the mixture stirred for 3 hours at room temperature, diluted with ethyl acetate, washed with dilute hydrochloric acid, and extracted with 5% aqueous solution of sodium hydrogen carbonate. The extract is acidified with hydrochloric acid and extracted with ethyl acetate. The extract is washed with water, dried, and evaporated to give a residue which is recrystallized from hexane to give cefalotin (227 mg) as free acid. Yield: 57%.

EXAMPLE 6

Cefazolin benzyl ester (544 mg) is hydrolyzed in a mixture of methylene chloride (50 ml) and nitrobenzene (50 ml) in the presence of anisole (650 mg) and aluminum chloride (400 mg) in a manner similar to that of Example 5 to give cefazolin (348 mg) as free acid. Yield: 77%.

EXAMPLE 7

N-Carbobenzoxycefalexin benzyl ester (1.07 g) is reacted for 2 hours in a mixture of nitromethane (40 ml) and methylene chloride (20 ml) in the presence of 6 mole equivalents of aluminum chloride and 6 mole equivalents of anisole. The reaction mixture is diluted with water and adjusted to pH 1.5 with hydrochloric acid. The aqueous layer is separated, washed with ethyl acetate and concentrated under reduced pressure. The residue is passed through a column of an adsorbent (Diaion HP-20; Mitsubishi Chemical Industries Ltd.). The adsorbent is washed with water and eluted with dilute ethanol. The eluate is concentrated to give crystals, which are collected by filtration and dried under reduced pressure to give cefalexin (0.64 g) as crude product. Yield: 88%.

EXAMPLE 8 p-Methoxybenzyl 7-phenylacetamidodeacetoxycephalosporanate (0.5 g) is treated with aluminum chloride (0.5 g) for 5 hours in a mixture of nitromethane (10 ml) and methylene chloride (10 ml) in a manner similar to that of Example 7, and the reaction mixture is worked up in a usual manner to give 7-phenylacetamidodeacetoxycephalosporanic acid (0.43 g). mp. 193°–196° C.

EXAMPLE 9 p-Chlorobenzyl 7-phenoxyacetamidodeacetoxycephalosporanate (0.5 g) is treated with aluminum chloride (0.42 g) in a mixture of nitrobenzene (20 ml) and carbon disulfide (40 ml) in a manner similar to that of Example 8 to give 7-phenoxyacetamidocephalosporanic acid (0.33 g). mp. 175°–177.5° C. Yield: 89%.

EXAMPLE 10

To a solution of triethylamine and penicillin V 1-oxide (0.32 g; prepared from penicillin V on treatment with peracetic acid) in N,N-dimethylformamide (3 ml) is added benzyl bromide (0.51 g), and the mixture reacted for 8 hours and then diluted with water to give the benzyl ester of penicillin V 1-oxide as crystals (1.05 g). This product (1.0 g) is refluxed with methanesulfonic acid (20 mg) for 4 hours in a mixture of benzene (8 ml) and N,N-dimethylacetamide (6 ml) to give benzyl 7-phenoxyacetamidodeacetoxycephalosporanate (0.64 g). mp 159°–160.2° C. To a solution of benzyl 7-phenoxyacetamidodeacetoxycephalosporanate (0.60 g) in a mixture of benzene (36 ml) and pyridine (0.15 g) is added phosphorus pentachloride (0.45 g) at 55° C. and the mixture stirred for 2 hours, mixed with methanol (70 ml), stirred for 1 hour, mixed with water (9 ml), and then stirred for 30 minutes. The aqueous layer, from which methanol is removed, is neutralized and extracted with ethyl acetate. The extract is concentrated and mixed with p-toluenesulfonic acid (0.27 g) to yield benzyl 7-aminodeacetoxycephalosporanate p-toluenesulfonate (0.57 g). mp. 152°–156° C. This salt (0.50 g) and triethylamine (0.11 g) are dissolved in methylene chloride (6 ml), and mixed with 1-ethoxycarbonyl-2-ethoxy-1,2-dihydroquinoline (0.29 g) and N-t-butoxycarbonylphenylglycine (0.27 g), and the mixture stirred for 7 hours. The reaction mixture is evaporated under reduced pressure, and the residue is dissolved in a mixture of ethyl acetate and 1 N-hydrochloric acid.

The organic layer is separated and washed with an aqueous solution of sodium hydrogen carbonate and then water, dried and evaporated under reduced pressure to give benzyl 7β-(N-t-butoxycarbonylphenylglycinamido)-deacetoxycephalosporanate (0.48 g). mp 145°-149° C. This is dissolved in a mixture of methylene chloride (4.5 ml) and nitromethane (9 ml) with anisole (0.58 g), mixed with aluminum chloride (0.72 g) under ice cooling, and stirred for 8 hours. The reaction mixture is diluted with water (32 ml), adjusted to pH 1.5, and the organic layer removed. The aqueous layer is washed with ethyl acetate and evaporated under reduced pressure. The residue (25 ml) is passed through a high porous polymer (Diaion HP-20 of Mitsubishi Chemical Industries Ltd.), and eluted with a mixture of methanol (14 ml) and water (26 ml). The eluate is concentrated under reduced pressure to give crude cefalexin (0.29 g). This is dissolved in dilute hydrochloric acid, and neutralized to pH 4 with ammonia under heating at 60° C., stirred for 5 hours, and cooled. The separated crystals are collected by filtration, washed with water, and dried to give cefalexin monohydrate (0.26 g). mp. 192° C.

EXAMPLE 11

Instead of penicillin V 1-oxide, penicillin G 1-oxide in treated in a manner similar to that of Example 10 to yield the same cefalexin monohydrate.

EXAMPLE 12

To a solution of benzyl 7β-(α-phenyl-α-p-methoxybenzyloxycarbonylacetamido)-3-methyl-1-oxadethia-3-cephem-4-carboxylate (1.10 g) in methylene chloride (24 ml) are added anisole (2.4 ml) and a solution of aluminum chloride (2.58 g) in nitromethane (12 ml) at 0° C. After stirring for 15 minutes at 0° C., the mixture is poured into a cold aqueous solution of 5% sodium hydrogen carbonate (100 ml), and the separated solid is filtered off. The filtrate is washed with methylene chloride (100 ml×2), acidified with 2 N-hydrochloric acid to pH 2.6, and passed through a column of high porous polymer adsorbent Diaion HP-20 (60 ml) sold by Mitsubishi Chemical Ind. Ltd. The column is washed with water (300 ml), and developed with methanol. After concentration of the eluate, the obtained residue is dissolved in methanol, treated with active carbon, and concentrated to give 7β-(α-phenyl-α-carboxyacetamido)-3-methyl-1-oxadethia-3-cephem-4-carboxylic acid (573 mg) as a colorless powder melting at 115°-120° C. with decomposition.

EXAMPLE 13

To a solution of benzyl 7β-(α-phenyl-α-carbobenzoxyaminoacetamido)-3-chloro-3-cephem-4-carboxylate (295 mg) in methylene chloride (6 ml) is added a solution of aluminum chloride (267 mg) in nitromethane (3 ml) under ice cooling. After stirring for 2 hours at room temperature, the mixture is diluted with ethyl acetate, washed with dilute hydrochloric acid, and extracted with an aqueous solution of 5% sodium hydrogen carbonate. The extract is acidified with hydrochloric acid and extracted with ethyl acetate. The extract is washed with water, dried, and evaporated. The residue is recrystallized from a mixture of ethyl acetate and ether to give 7β-(α-phenyl-glycinamido)-3-chloro-3-cephem-4-carboxylic acid (167 mg). Yield: 91.4%.

EXAMPLE 14

(1) To a mixture of sodium hydroxide (13.0 g) in water (14.2 g) and benzene (300 ml) is added D-phenylglycin (45.0 g), and the mixture is stirred at 76° C. for 10 minutes. Then α-acetyl-γ-butyrolactone (45 ml) is added to the mixture at 60° C. and the mixture is refluxed for 6 hours while removing formed water. After concentration under reduced pressure, the mixture is dissolved in acetone (300 ml) and added dropwise to cold ether (5 L) during 30 minutes. After 10 minutes, the mixture is filtered to collect the separated crystals, which are washed with ether (500 ml) and dried to give the enamine of phenylglycin and α-acetyl-γ-butyrolactone (82.42 g). Yield: 97.74%.

(2) To a solution of benzyl 7β-phenoxyacetamidodeacetoxycephalosporanate (50 g) in benzene (1.5 L) are added pyridine (16.05 ml) and phosphorus pentachloride (35.6 g) at 50° C. in nitrogen. After stirring for 2 hours, the mixture is cooled with ice-water, and mixed with cold isobutanol (750 ml). After stirring for 1 hour at room temperature, the mixture is cooled to 10° C., diluted with cold water (750 ml), and stirred at room temperature for 30 minutes. The reaction mixture is concentrated, dissolved in a mixture of benzene (400 ml) and water (100 ml), and shaken. The benzene layer is acidified with 2 N-hydrochloric acid (50 ml×2), and the aqueous layer separated and washed with benzene (200 ml). The aqueous layer is covered with ethyl acetate (1 L), adjusted with 2 N-sodium hydroxide to pH 6.5, shaken, and the organic layer separated. The layer is concentrated under reduced pressure, mixed with toluene (70 ml) and filtered to collect benzyl 7β-aminodeacetoxycephalosporanate (32.06 g). mp. 129°-130° C. Yield: 92.37%.

(3) A solution of the product in (2) above (20.0 g) in methylene chloride (150 ml) at −33° is added to a solution of the mixed anhydride of phenylglycin [prepared from the enamine of D-phenylglycin and α-acetyl-γ-butyrolactone prepared in (1) above (29.72 g) and ethyl chloroformate (8.64 ml) in ethyl acetate (225 ml) in the presence of N-methylmorpholine (0.435 ml) at −35° C. during 10 minutes], and kept at −33° C. for 1 hour, 0° C. for 1 hour and 20° C. for 0.5 hours. The reaction mixture is concentrated under reduced pressure, dissolved in ethyl acetate (150 ml) at 55° C., and cooled to 3° C. to separate crystals, which are collected by filtration, washed with cold ethyl acetate (90 ml), and water, and dried to give cefalexin benzyl ester, the amino of which is protected in the form of the enamine with α-acetyl-γ-butyrolactone (34.28 g). mp. 232°-238° C. (decomposition). Yield: 95.27%.

(4) To a solution of the product obtained in the above (3) in anisole (112.5 ml) is added powdered aluminum chloride (21.9 g) at 3° C., and the mixture is stirred for 8 hours at room temperature. After one night, the mixture is cooled with ice water, and water (415 ml) is added dropwise to the mixture. The mixture is mixed with concentrated hydrochloric acid (10 ml), stirred at room temperature for 10 minutes, filtered through a layer of Hyflo super cell, and the aqueous layer separated. The layer is washed with methylene chloride (100 ml), mixed with 4 N-sodium hydroxide (pH 3.0), and adsorbed in a column of high porous polymer HP-20 (500 ml). After washing with water until obtaining negative aluminum ion, the column is washed with 30% acetone acidified with concentrated hydrochloric acid to pH 1 (850 ml). The eluates containing cefalexin are concentrated at below 30° C. to 30 g, diluted with N,N-dimethylformamide (100 ml), neutralized with concentrated aqueous ammonia (2.8 ml) to pH 6.9 to separate crystals, cooled with ice-water for 30 minutes, and filtered to collect the crystals. The crystals are washed with N,N-dimethylformamide (20 ml), and ethyl acetate (25 ml×2) and dried to give a complex of N,N-dimethylformamide and cefalexin (2:1). Yield: 60.65%, 12.30 g.

In another run, cefalexin is formed in 84.7% yield in the reaction mixture and crystallized in 77.5% yield.

EXAMPLE 15

To a solution of N-t-butoxycarbonyl-L-phenylalanine benzyl ester (1 g) in methylene chloride (10 ml) is added aluminum chloride (1 g) in anisole (12 ml), and the mixture is stirred at room temperature for 2 hours. The reaction mixture is poured into an aqueous sodium hydrogen carbonate solution and filtered to remove insoluble material. The filtrate is washed with methylene chloride, acidified to pH 2.5 with hydrochloric acid, and adsorbed on high porous polymer HP-20 (manufactured by Mitsubishi Chemical Co., Ltd.). After washing with water, the resin is washed with methanol. Concentration of the methanol eluent gives crystals of L-phenylalanine (0.3 g) melting at 270° C. Yield: 54%.

EXAMPLE 16

To a solution of benzyl 2-p-isobutylphenylpropionate (3 g) in methylene chloride (18 ml) are added a solution of aluminum chloride (4 g) in nitromethane (50 ml) and anisole (3 ml) at 0° C., and the mixture is stirred at room temperature for 6 hours. The reaction mixture is diluted with ethyl acetate, washed with hydrochloric acid and water, dried and evaporated. The residue is recrystallized with n-hexane to give 2-p-isobutylphenylpropionic acid (186 mg) melting at 75°–77.5° C. Yield 91%.

EXAMPLE 17

A mixture of 3-phenylacetamido-1-(α-carbobenzoxy-p-hydroxybenzyl) azetidin-2-one (15 mg), methylene chloride (0.5 ml), aluminum chloride (12 mg) and anisole (0.2 ml) is kept at −20° C. for 8 hours. The reaction mixture is diluted with ethyl acetate, washed with dilute hydrochloric acid and water, dried, and concentrated in vacuo. Crystallizing the residue from a mixture of ethyl acetate and ether gives 3-phenylacetamido-1-(α-carboxy-p-hydroxybenzyl)azetidin-2-one (9 mg) melting at 134°–141° C. Yield: 75%.

EXAMPLE 18

A mixture of benzyl phenylacetate (218 mg), methylene chloride (2 ml), aluminum chloride (357 mg), and nitromethane (1 ml) is stirred for 1 hour under ice cooling. The mixture is acidified with cold dilute hydrochloric acid and extracted with methylene chloride. The organic layer is extracted again with 5% aqueous sodium hydrogen carbonate solution. The aqueous extract is acidified with hydrochloric acid, and extracted with ethyl acetate. The organic layer is dried over sodium sulfate and concentrated to give phenylacetic acid (114 mg) melting at 77° C. Yield: 87%.

The invention being thus described, it will be obvious that the same may be varied in many ways. Such variations are not to be regarded as a departure from the spirit and scope of the invention, and all such modifications are intended to be included within the scope of the present invention.

What we claim is:

1. A process for preparing a free carboxylic acid from a benzyl alcohol ester which comprises treating a carboxylate of benzyl alcohol or a carboxylate of a benzyl alcohol substituted by $C_1$ to $C_5$ alkyl, $C_1$ to $C_5$ alkoxy, $C_5$ to $C_{10}$ aryloxy, $C_1$ to $C_{12}$ acyloxy, hydroxy, $C_1$ to $C_5$ alkylamino, $C_1$ to $C_8$ acylamino, amino, carboxy, $C_2$ to $C_6$ carbalkoxy, carbamoyl, or halogen, with a Lewis acid selected from at least one member of the group consisting of boron trihalides, titanium tetrahalides, zirconium tetrahalides, tin tetrahalides, antimony halides, bismuth trichloride, aluminum trihalides, zinc halides, ferric halides and zinc sulfate, in a solvent at a temperature of from about −10° C. to 100° C.

2. The process of claim 1, wherein the resulting product is hydrolyzed.

3. The process of claim 1, wherein said ester is a benzyl ester of a cephalosporin.

4. The process of claim 3, wherein the resulting product is hydrolyzed.

5. The process of claim 1, wherein the Lewis acid is selected from at least one member of the group consisting of aluminum chloride, titanium tetrachloride, tin tetrachloride, boron trifluoride, and zinc chloride.

6. The process of claim 1, wherein the benzyl ester is selected from at least one member of the group consisting of a chlorobenzyl ester, bromobenzyl ester, $C_1$ to $C_3$ alkoxybenzyl ester, $C_1$ to $C_3$ alkylbenzyl ester, and an unsubstituted benzyl ester.

7. The process of claim 1, wherein the reaction is carried out in a solvent selected from the group consisting of nitromethane, carbon disulfide, methylene chloride, anisole and mixtures thereof.

8. The process of claim 1, wherein the reaction is carried out in the presence of a carbonium ion acceptor.

9. The process of claim 8, wherein the reaction is carried out in the presence of anisole.

10. The process of claim 1, wherein the reaction is carried out at from about 0° C. to 40° C.

11. The process of claim 2, wherein the hydrolysis is carried out with an aqueous mineral acid.

* * * * *